(12) United States Patent
Smith

(10) Patent No.: US 9,504,482 B2
(45) Date of Patent: Nov. 29, 2016

(54) GUIDE FOR DRILLING AN IRREGULAR-SHAPED BODY

(75) Inventor: Graham Smith, Newburyport, MA (US)

(73) Assignee: Smith & Nephew, Inc., Memphis, TN (US)

(*) Notice: Subject to any disclaimer, the term of this patent is extended or adjusted under 35 U.S.C. 154(b) by 107 days.

(21) Appl. No.: 13/098,930

(22) Filed: May 2, 2011

(65) Prior Publication Data

US 2011/0270255 A1    Nov. 3, 2011

Related U.S. Application Data

(60) Provisional application No. 61/329,994, filed on Apr. 30, 2010.

(51) Int. Cl.
*A61B 17/16* (2006.01)
*A61B 17/17* (2006.01)

(52) U.S. Cl.
CPC .... *A61B 17/1684* (2013.01); *A61B 2017/1778* (2013.01)

(58) Field of Classification Search
CPC .... A61B 17/16; A61B 17/164; A61B 17/17; A61B 17/1717; A61B 17/1721; A61B 17/1728; A61B 17/175; A61B 17/1753; A61B 17/7082; B25B 23/08; B25B 23/10; B25B 23/101; B25B 23/105; B25B 23/108; B25B 23/106; B25B 23/12; B25B 27/00
USPC .............. 606/80, 89, 96–98, 103, 104, 208; 81/90.2–90.5, 91.3, 112–115, 81/345–351, 383.5, 443–447, 453–455
See application file for complete search history.

(56) References Cited

U.S. PATENT DOCUMENTS

| | | | | |
|---|---|---|---|---|
| 86,016 A | * | 1/1869 | Howell | A61B 17/29 606/127 |
| 3,604,487 A | * | 9/1971 | Gilbert | 81/443 |
| 4,363,250 A | * | 12/1982 | Suga | B25B 23/10 81/453 |
| 4,721,116 A | * | 1/1988 | Schintgen | A61B 10/02 600/564 |
| 4,896,663 A | * | 1/1990 | Vandewalls | A61B 17/175 269/236 |

(Continued)

FOREIGN PATENT DOCUMENTS

| | | |
|---|---|---|
| EP | 1588669 A1 | 10/2005 |
| WO | WO2008139260 A2 | 11/2008 |
| WO | WO2009098086 A1 | 8/2009 |

OTHER PUBLICATIONS

Invitation to pay Additional Fees for PCT/US2011/034736 dated Jul. 19, 2011.

(Continued)

*Primary Examiner* — Matthew Lawson
*Assistant Examiner* — Amy Sipp
(74) *Attorney, Agent, or Firm* — Burns & Levinson LLP; Joseph M. Maraia

(57) ABSTRACT

The present invention provides a surgical instrument for guiding a drill into bone, the surgical instrument comprising; an elongate body comprising a shaft having a handle towards its proximal end and a head towards its distal end, wherein the head comprises a mouth and jaw assembly, and the shaft comprises a lumen aligned with the longitudinal axis of the shaft and extending from the proximal end of the surgical instrument to the mouth of the shaft, wherein the lumen is suitable for receipt and passage of a drill, and the jaw assembly comprises a pair of opposed reciprocating arms.

34 Claims, 10 Drawing Sheets

(56) References Cited

U.S. PATENT DOCUMENTS

| | | | | |
|---|---|---|---|---|
| 5,409,490 | A | * | 4/1995 | Ethridge ............ A61B 17/8605 606/80 |
| 5,667,513 | A | * | 9/1997 | Torrie et al. ................... 606/104 |
| 5,776,075 | A | * | 7/1998 | Palmer ................... A61B 10/06 600/564 |
| 5,820,630 | A | * | 10/1998 | Lind ....................... A61B 10/06 606/205 |
| 6,024,708 | A | * | 2/2000 | Bales et al. .................... 600/564 |
| 6,123,678 | A | * | 9/2000 | Palmer ................... A61B 10/06 600/567 |
| 6,129,683 | A | * | 10/2000 | Sutton .................... A61B 10/06 600/564 |
| 6,508,496 | B1 | * | 1/2003 | Huang ...................... E01H 1/12 294/115 |
| 6,582,451 | B1 | * | 6/2003 | Marucci ................. A61B 17/29 606/207 |
| 6,656,205 | B1 | * | 12/2003 | Manhes ................. A61B 17/29 606/205 |
| 6,701,812 | B1 | * | 3/2004 | Sawamura .............. B25B 23/10 81/452 |
| 7,341,564 | B2 | * | 3/2008 | Zwiefel .................. A61B 10/06 600/564 |
| 7,351,201 | B2 | * | 4/2008 | Ouchi ................. A61B 1/00087 600/104 |
| 7,871,422 | B2 | * | 1/2011 | Shibata .................. A61B 10/06 606/205 |
| 7,985,239 | B2 | * | 7/2011 | Suzuki ............... A61B 10/0096 606/205 |
| 2005/0027299 | A1 | | 2/2005 | Metzger |
| 2005/0113841 | A1 | * | 5/2005 | Sheldon ............. A61B 17/1668 606/88 |
| 2005/0245934 | A1 | * | 11/2005 | Tuke ..................... A61B 17/15 606/79 |
| 2007/0233136 | A1 | * | 10/2007 | Wozencroft ......... A61B 17/175 606/86 R |
| 2007/0244508 | A1 | * | 10/2007 | Weizman ............... A61B 10/06 606/205 |
| 2007/0276370 | A1 | | 11/2007 | Altarac et al. |
| 2008/0027435 | A1 | | 1/2008 | Zucherman et al. |
| 2009/0048673 | A1 | | 2/2009 | Le Huec |
| 2009/0254093 | A1 | * | 10/2009 | White .................. A61B 17/175 606/89 |
| 2010/0030116 | A1 | * | 2/2010 | Chana .................... A61B 5/103 600/587 |
| 2010/0137924 | A1 | * | 6/2010 | Tuke .................... A61B 17/175 606/86 R |
| 2010/0292743 | A1 | * | 11/2010 | Singhal ................ A61B 17/175 606/86 R |
| 2013/0085494 | A1 | | 4/2013 | Weisenburgh, II et al. |

OTHER PUBLICATIONS

International search report and written opinion for PCT-US2011/034736 mailed on Oct. 12, 2011.
International Preliminary Report on Patentability, PCT/US2011/034736, Nov. 6, 2012, 9 pgs.
Communication pursuant to Article 94(3) EPC, EP11720354.7, Dec. 12, 2013, 2 pgs.
Communication pursuant to Article 94(3) EPC for EP11720354.7 mailed on Jan. 26, 2015, 3 pgs.
Notice of reasons for rejection for JP 2013-508079 mailed on Dec. 8, 2014, 6 pgs.
Decision of Rejection for related Japanese Patent Application No. 2013-508079 mailed Nov. 2, 2015.
Patent Examination Report No. 1 from related Australian Application No. 2011245143 mailed Jun. 24, 2015.
Second Office Action for Chinese Patent Application No. 201180032468.3 dated May 7, 2015.
Communication pursuant to Article 94(3) from related European Application No. 11720354.7 mailed Feb. 22, 2016.
Patent Examination Report No. 2 for related Australian Application No. 2011245143 issued Mar. 2, 2016.

* cited by examiner

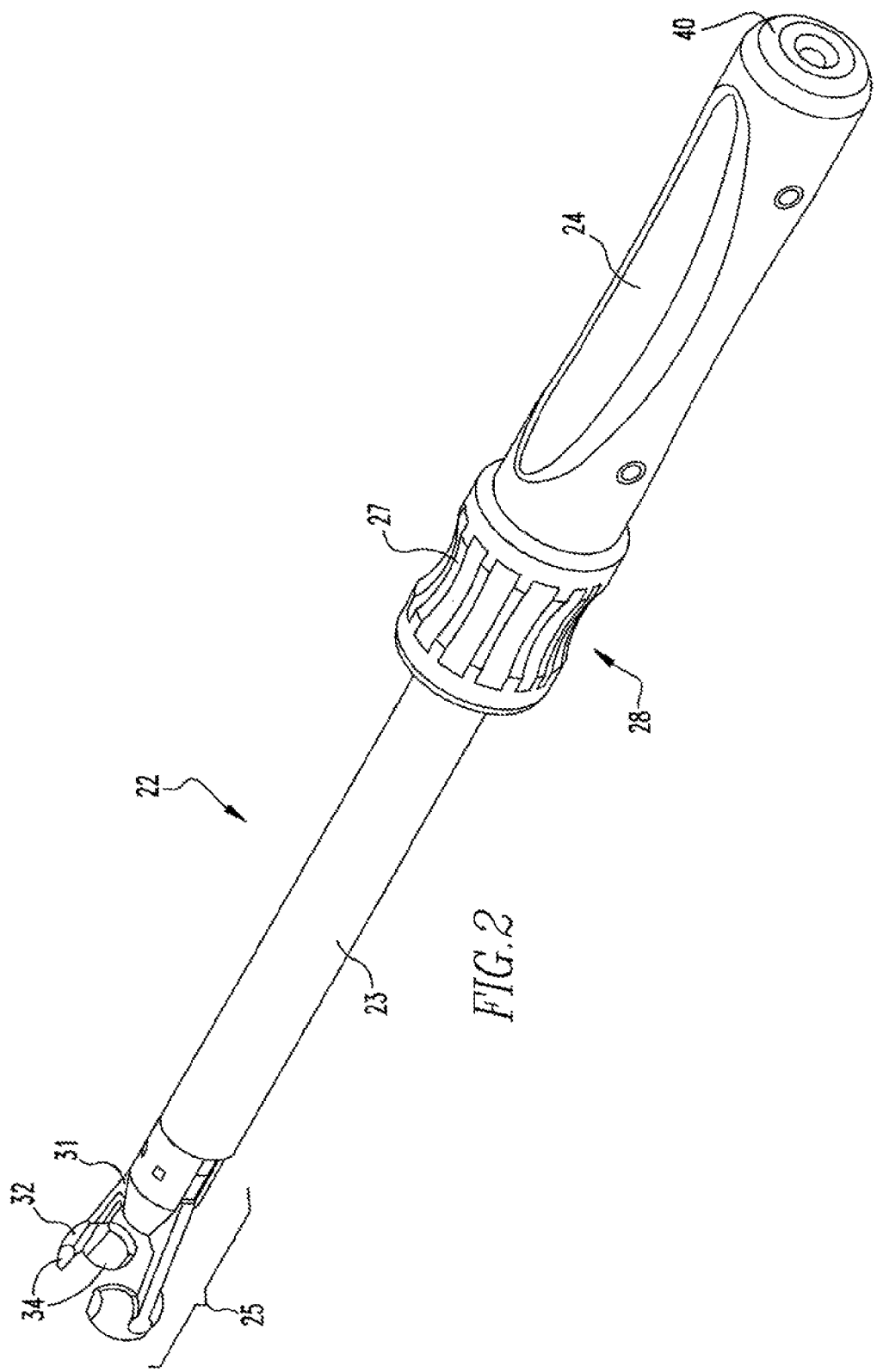

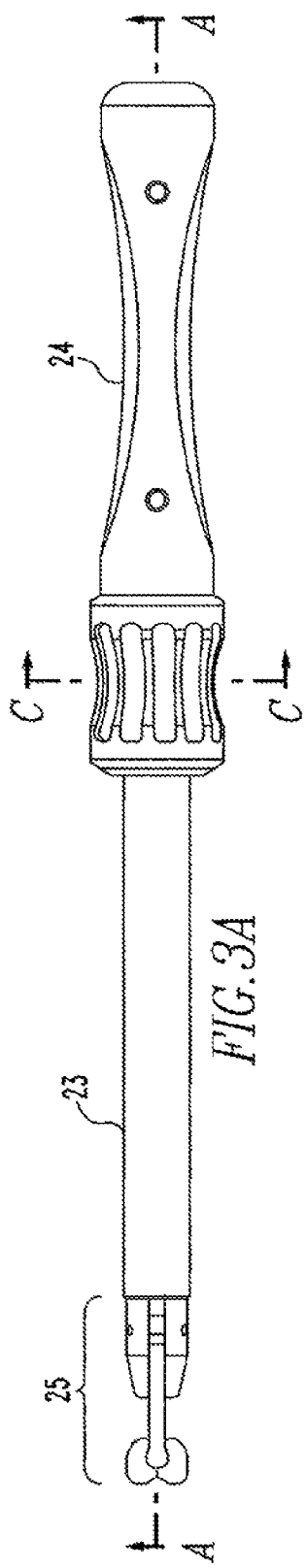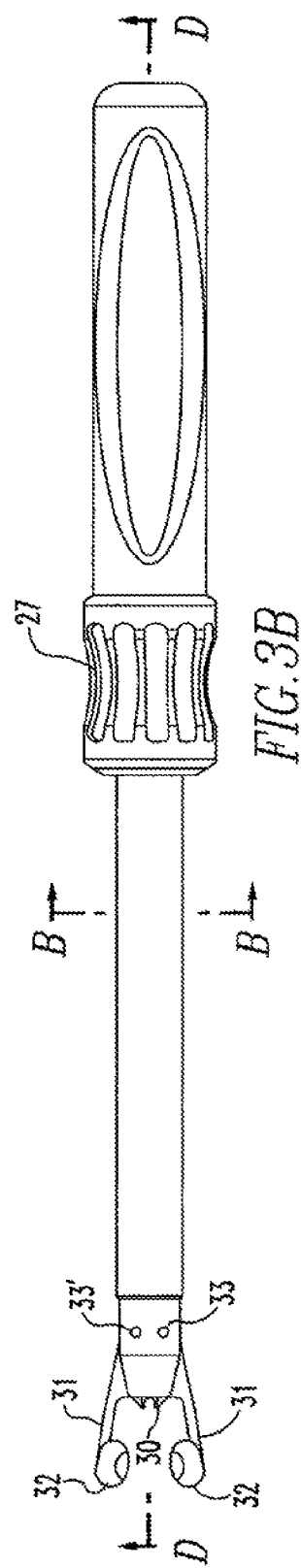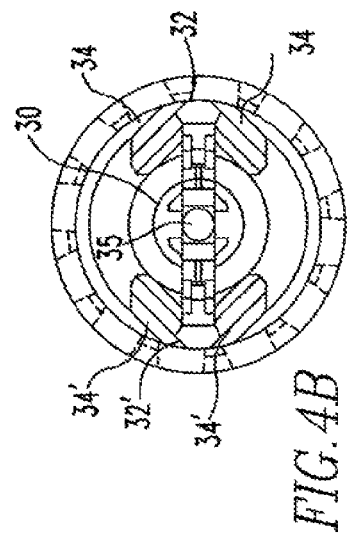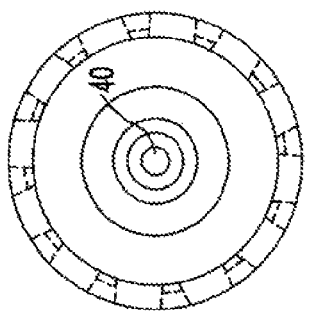

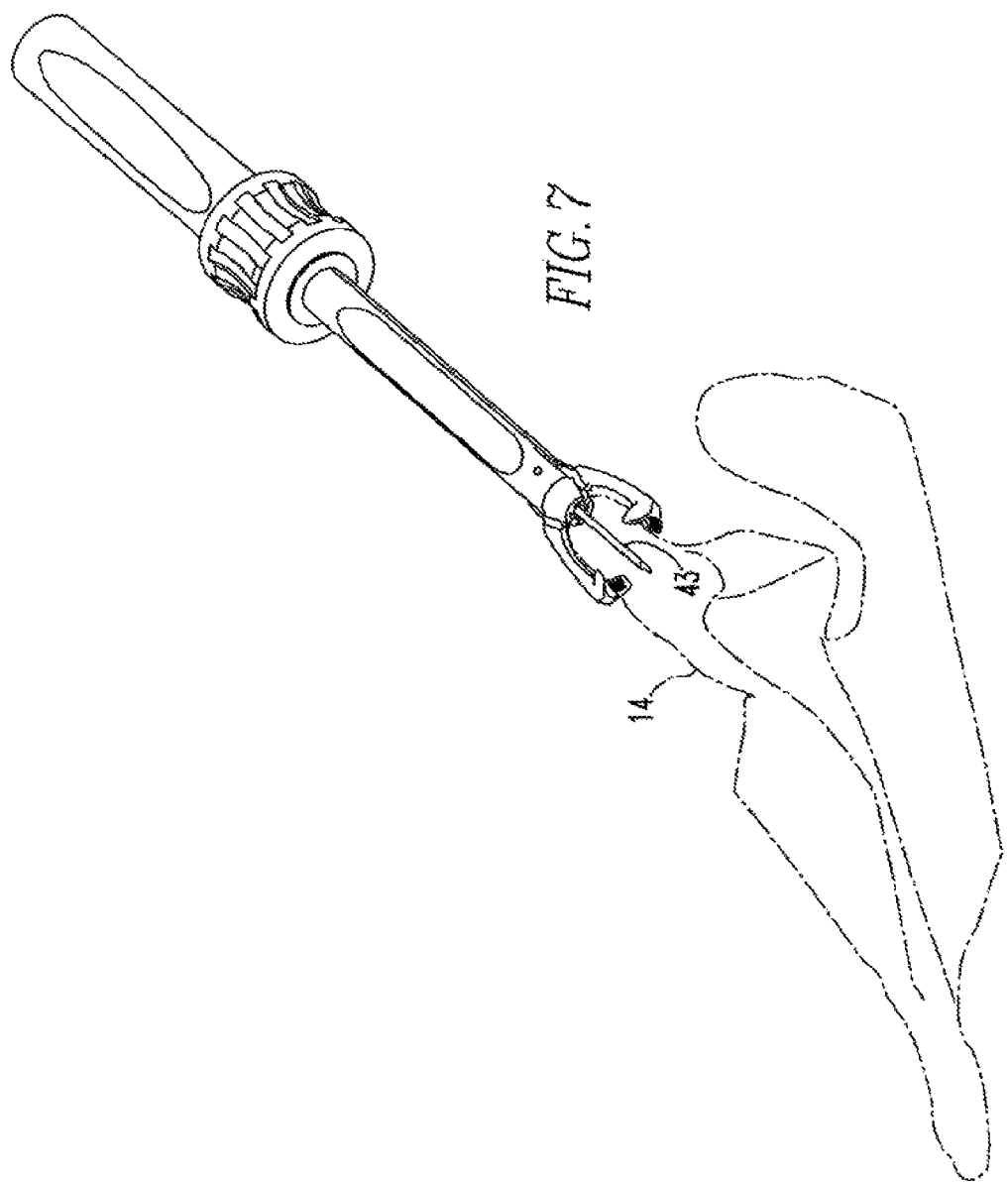

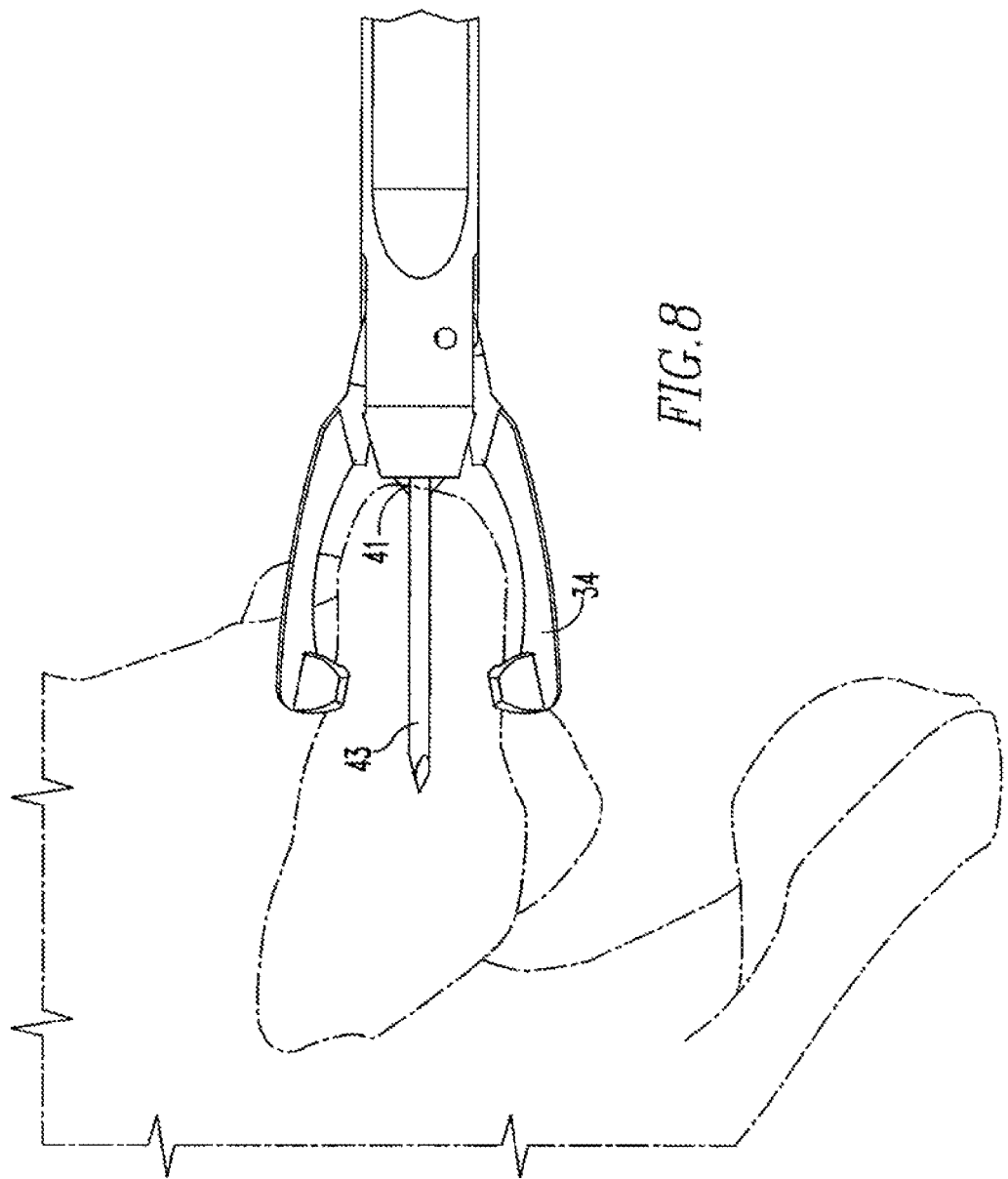

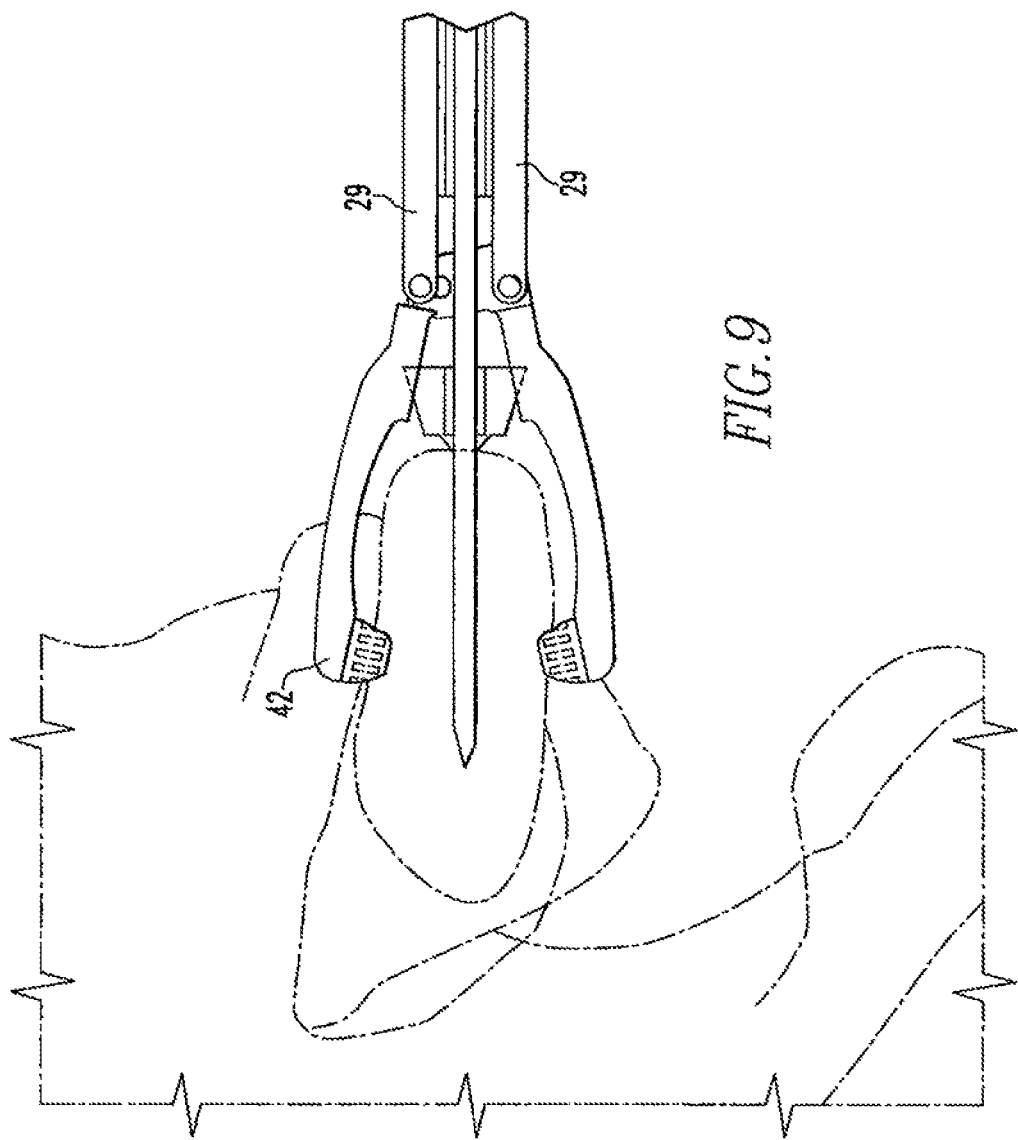

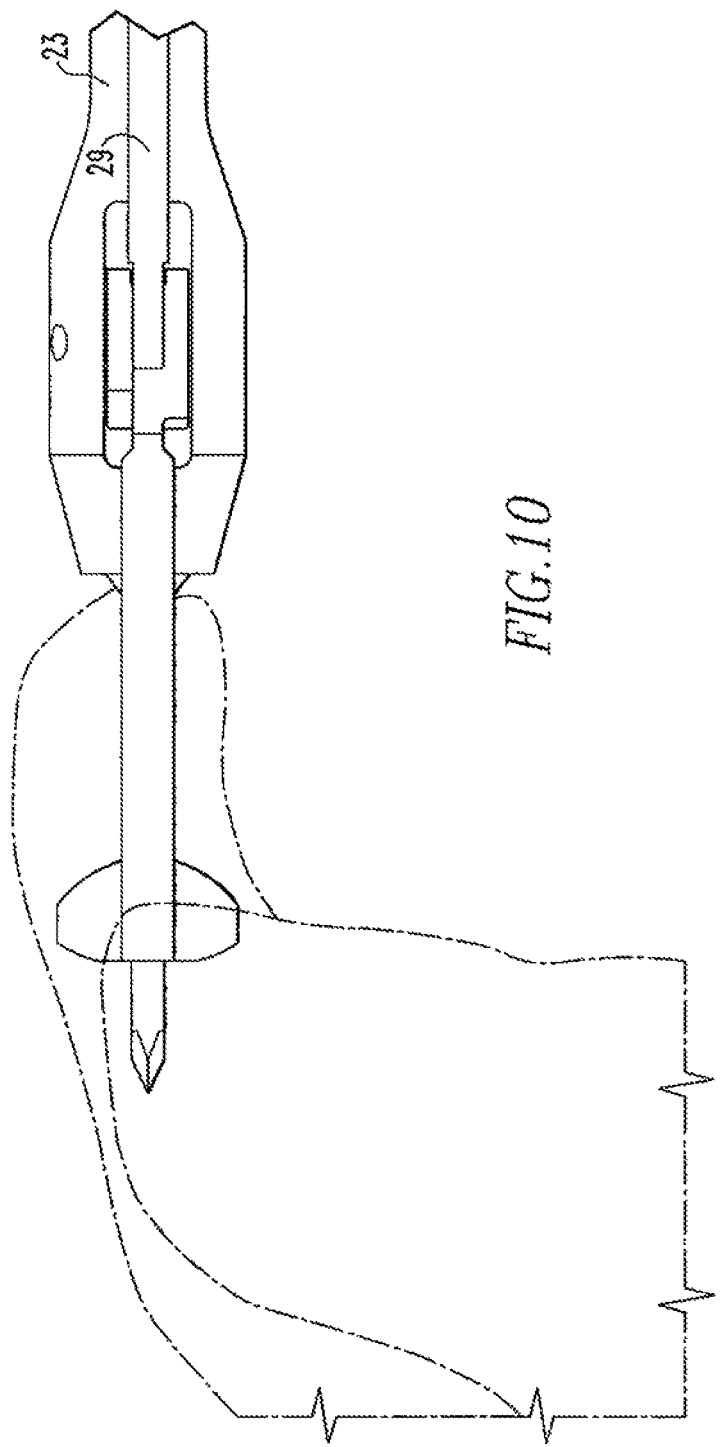

_US 9,504,482 B2_

GUIDE FOR DRILLING AN IRREGULAR-SHAPED BODY

CROSS-REFERENCE TO RELATED APPLICATION

This application claims priority to U.S. Patent Application Ser. No. 61/329,994, the disclosure of which is incorporated herein by reference in its entirety.

BACKGROUND

Field of Technology

The present invention concerns a surgical drill-guide. In particular, the present invention relates to a surgical guide for drilling an irregular-shaped body.

Related Art

The shoulder is a ball and socket joint made up of the clavicle, the scapula and the humerus, and associated muscles, ligaments and tendons. It is formed by the articulation between the medial anterior surface of the head of the humerus and the glenoid fossa of the scapula. The shallowness of the fossa and relatively loose connections between the shoulder and the rest of the body provides the arm with a huge range of motion, and make it an extremely mobile joint. The shoulder can abduct, adduct, rotate, be raised in front of and behind the torso, and move through a complete cycle in the sagittal plane.

However, this tremendous mobility makes the shoulder quite unstable and far more prone to dislocation and injury than most other joints in the body.

The shoulder joint is stabilised by the shoulder capsule and a ring of cartilage surrounding the glenoid, which is known as the shoulder labrum. The capsule is formed by a series of ligaments which connect the humerus to the glenoid. When the labrum and/or ligaments have torn or where the ligaments have been hyper-extended, the shoulder becomes unstable and will naturally have a greater tendency to dislocate. This instability can lead to further shoulder problems and, in particular, dislocation and subluxation—where the joint is hyper-mobile but does not dislocate. As a result of shoulder instability it is more likely that repeated dislocations or subluxations will occur during active movement or exercise.

Instability of the shoulder can be caused by a traumatic dislocation, atraumatic dislocation or a non-traumatic dislocation.

Traumatic dislocation occurs when the shoulder is subjected to an adverse force which is sufficient to pull the shoulder out of joint. This can occur through a sporting injury or a traumatic accident such as experienced in a road traffic accident. Due to the large forces associated with such an injury, the labrum can be torn from the bone, creating a Bankart lesion, and this can result in an unstable shoulder. Such an injury can lead to subsequent episodes of dislocation.

An atraumatic dislocation occurs when the shoulder is dislocated through only a nominal force, such as when reaching upwards or when turning in bed. In most cases, the shoulder will relocate itself with a little help. This type of dislocation is relatively common in people with hyper-flexible joints and is associated with certain orientations in the arms of sufferers. This over-flexibility of the joint is generally associated with the way in which the muscles around the shoulder interact with each other, which can produce an imbalance in the control of the joint. In some cases, these problems can be overcome with physiotherapy.

In addition, in a limited number of people their shoulders can undergo positional non-traumatic dislocation. The shoulders of sufferers of this condition are so loose that they can simply 'fall' out of joint. This type of dislocation is usually painless and can be relocated easily. Typically, both shoulders are involved and dislocation usually occurs as a result of abnormal muscle function in which the shoulder is pulled out of joint when it is moved in a particular direction. Dislocation can occur with innocuous movements such as when lifting the arm above the head and to the side or forwards. Again, physiotherapy can help to correct this problem by synchronising the muscles to work correctly.

Occasionally, in instances of repeated dislocation and/or subluxation, the problem can generally only be remedied through surgery.

In surgery to correct shoulder abnormalities or injury it is sometimes necessary to drill into or through an irregular-shaped body. For example, in a Latarjet shoulder procedure approximately 15 mm of the tip of the coracoid process is transferred, along with the conjoined tendon, to the glenoid rim. This forms an extension of the glenoid surface and produces a restraint to the shoulder which helps to prevent further dislocation.

During the Latarjet procedure the coracoid process is divided at its base with the coraco-acromial ligament and the conjoined tendon. The pectoralis minor muscle is released from the coracoid process, the subscapularis muscle is split and the capsule of the shoulder joint opened to expose the front of the glenoid. After the glenoid has been prepared, the coracoid is attached and the coraco-acromial ligament is used to strengthen the joint capsule.

In movements involving the arm being lifted above the head (abduction and rotation), the muscles which are relocated over the subscapularis act to prevent dislocation of the shoulder joint.

A critical element of this procedure is the drilling of a hole along the central axis of the coracoid process. This allows a screw to be driven down the centre of the coracoid and into the glenoid to secure the graft thereto (FIG. 1). During this process it is crucial that the position of the graft is held securely and that the graft does not split.

During the procedure the surgeon is able to view the tip of the coracoid, and hence the starting point of the drill, but the position of the drill once it enters the tip is determined purely through guesswork by the surgeon estimating its direction of travel. This is especially true when the procedure is performed arthroscopically as the surgeon's view of the anatomy at the surgical site is by means of a monitor, and rendered in two dimensions. This is not ideal and can lead to fractures in the graft and subsequent problems with its attachment to the glenoid.

The present invention seeks to overcome the above issues by providing a drill-guide for use with an irregular-shaped body.

SUMMARY

In a first aspect, the present invention provides a surgical instrument for guiding a drill into bone, the surgical instrument comprising; an elongate body comprising a shaft having a handle towards its proximal end and a head towards its distal end, wherein the head comprises a mouth and jaw assembly, and the shaft comprises a lumen aligned with the longitudinal axis of the shaft and extending from the proximal end of the surgical instrument to the mouth of the shaft, wherein the lumen is suitable for receipt and passage of a drill, and the jaw assembly comprises a pair of opposed reciprocating arms.

Preferably, the mouth further comprises engaging means suitable for engaging with tissue such as bone. Preferably, the engaging means are located at the periphery of the mouth. Suitably, the engaging means comprise one or more teeth; preferably, a plurality of teeth. In use, these teeth engage with bone, for example the end of the coracoid process, to help locate the instrument and prevent slippage. Preferably, the teeth are sharpened.

Preferably, the pair of opposed reciprocating arms are operable in a plane which passes through the longitudinal axis of the shaft.

Optionally, the jaw assembly further comprises a second pair of opposed reciprocating arms. Preferably, the second pair of arms are operable within a plane which passes through the longitudinal axis of the shaft. Preferably, the two pairs of arms of the jaw assembly are operable in different planes. More preferably, the two pairs of arms of the jaw assembly are operable in substantially perpendicular planes.

Suitably, the jaw assembly is operable between a first, open, position and a second, substantially closed, position, and suitably positions therebetween.

Suitably, the arms of the jaw assembly can be curved. Preferably, one or both of the arms can have sharpened distal tips.

Alternatively, one arm of each pair of jaws can have a sharpened distal tip, and the second arm comprises a paddle. Further alternatively, each arm comprises a paddle at their respective distal ends. Other suitable shapes and designs of the arms can be used.

Suitably, each paddle includes one or more inwardly facing projections. Suitably, the inwardly facing projections are substantially perpendicular to the longitudinal axis of the shaft, when the jaw assembly is in a substantially closed position. The inwardly facing projections assist the jaws in engaging and securing the instrument to a bone surface to be drilled. In particular, the projections help to grip the distal tip of the coracoid process and centre the instrument prior to drilling.

Preferably, the paddles collectively form an opening, coaxially with the longitudinal axis of the shaft, when the jaw assembly is substantially closed, or attached to tissue or bone and between the first and second positions. More preferably, the inwardly facing projections form the opening. Preferably, the opening has a non-continuous border. Suitably, the inwardly facing projections have a U- or V-shaped cross-section in a plane substantially perpendicular to the longitudinal axis of the shaft, when the jaw assembly is in the second, substantially closed, position. Preferably, the paddles are anatomically shaped for engagement with and to grip bone.

The opening provided by the paddles allows the distal end of a drill or drill-bit, which has been passed through the lumen from the proximal end of the surgical instrument and which exits the mouth, to pass through and beyond the jaw assembly, if required. This is important in situations where a surgeon wishes to drill beyond the reach of the closed jaw assembly.

Suitably, the inner surfaces of the paddles comprise a gripping surface which can include a series of studs, serrations or ribs, or a combination thereof. Preferably, the inner surfaces of the inwardly facing projections comprise ribs a gripping surface which can include a series of studs, serrations or ribs or a combination thereof. The gripping surface enhances the engagement of the instrument with the bone surface.

Preferably, the jaw assembly further comprises a lock to lock the jaw assembly in the first or second position, or a position therebetween. Suitably, the lock comprises a ratchet, locking screw or is achieved by means of the mechanical advantage of a screw thread. Any other means to suitably lock the jaw assembly can be used. Preferably, the lock is self-locking; more preferably, self-locking and which locks itself when the jaw assembly is closed around an object, such as tissue or bone. The lock helps to prevent movement of the instrument, and thus the drill, when drilling. The self-locking feature makes the instrument easy to use, and particularly suitable for arthroscopic procedures.

Suitably, the handle comprises actuating means for moving the jaw assembly between the first, open, position and the second, substantially closed, position, and positions therebetween. Suitably, the actuating means comprises one or more rods which move the arms of the jaw assembly incrementally between the first and second positions. Preferably, the actuating means comprises a pair of rods. Suitably, the rod or rods are drivable, in use, by one or more levers in the form of a hand- or pistol-grip. Suitably, the hand or pistol-grip includes a ratchet mechanism. Alternatively, the rod or rods are pivotally connected with a threaded boss and are drivable, in use, by a rotary knob, having an inner surface including a mating screw thread that is complementary with that of the threaded boss, and in which the rotary knob is co-axially aligned with the lumen of the device. Preferably, the rotary knob is mounted co-axially with the handle. Other suitable means for moving the jaw assembly can be used. For example, the jaw assembly can be actuated by one or more cables.

The arrangement of the handle and actuating means facilitate one-handed operation of the instrument so that it can be used in arthroscopic procedures.

In a second aspect of the present invention, there is provided a kit comprising a surgical instrument according to the first aspect; and a drill.

Preferably, the drill is retractable. Preferably, the drill has distal and proximal ends and is engageable with a powered drive-unit at its proximal end. Preferably, the drill is moveable from a first position, in which the distal end of the drill is located in the shaft, to a second position, in which the distal end of drill extends from the mouth. Preferably, the drill comprises a depth gauge or stop. The depth gauge or stop helps to prevent a surgeon from drilling too deeply.

BRIEF DESCRIPTION OF THE DRAWINGS

The above and other aspects of the invention will now be described with reference to the following drawings in which:

FIG. 2 is an embodiment of a drill-guide according to the invention;

FIGS. 3A-B are, respectively, side and top plan views of the drill-guide of FIG. 1;

FIGS. 4A-B are, respectively, proximal end and distal end views of the drill-guide of FIG. 1;

FIG. 7 is a perspective view of the drill-guide of FIG. 1, attached to the coracoid process, and also including a drill;

FIG. 8 is a plan view of the distal end of the drill-guide and drill of FIG. 7;

FIG. 9 is a sectional view through the longitudinal axis of the drill-guide of FIG. 8;

FIG. 10 is a side view of the distal end of the drill-guide and drill of FIG. 7;

DETAILED DESCRIPTION OF THE EMBODIMENTS

Figure 1:
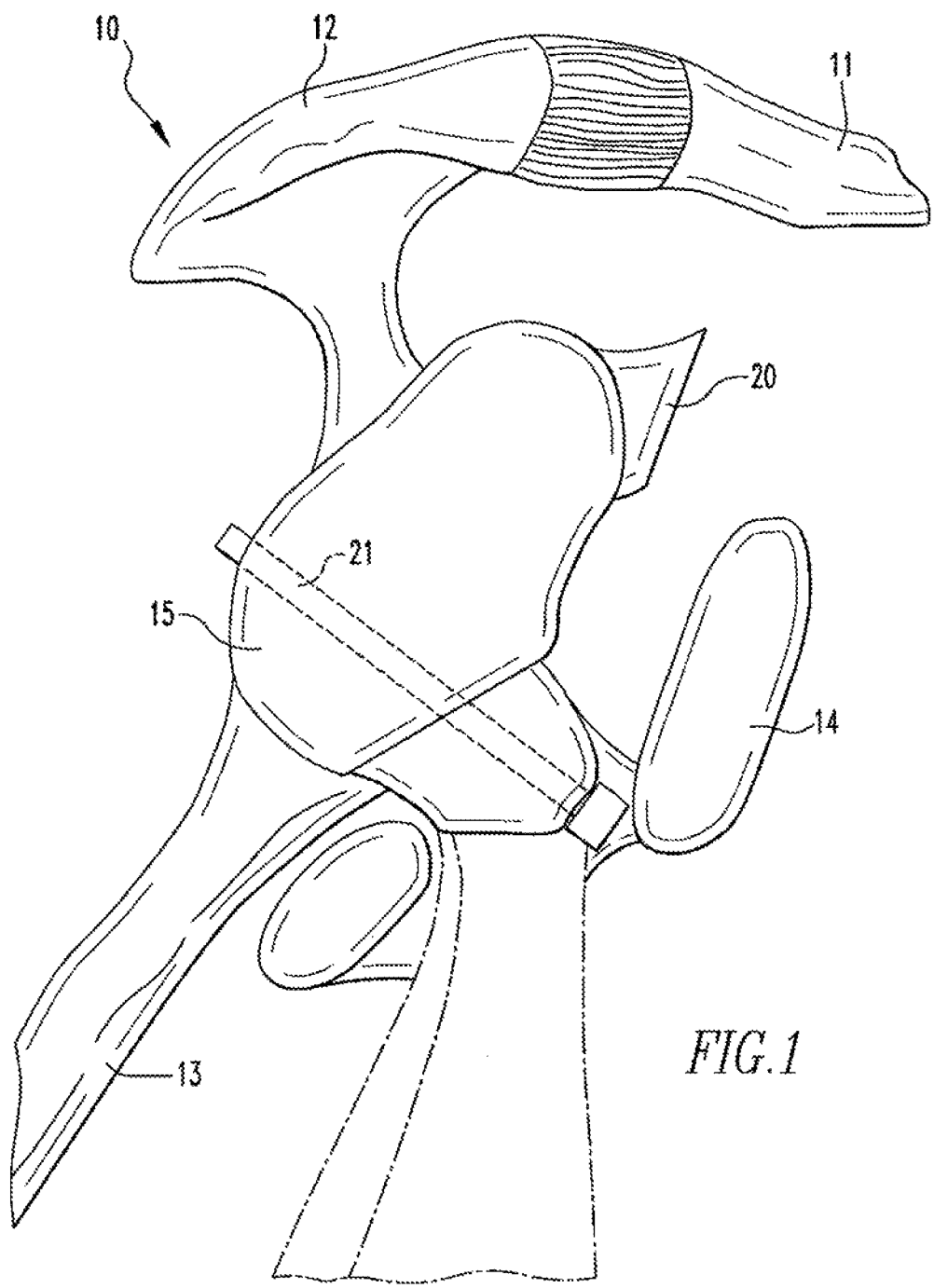
FIG. 1 is an lateral view of a right shoulder in which the tip of the coracoid process has been transferred and secured, along with the conjoined tendon, to the glenoid rim.
Figure 5A:
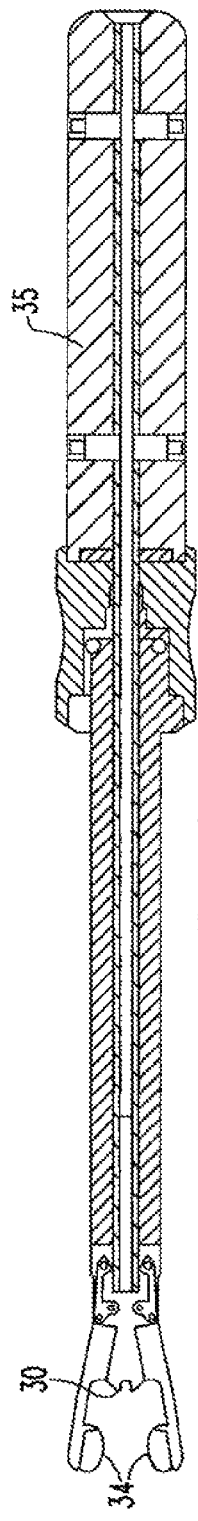
FIGS. 5A-B are sectional views along the lines A-A and D-D of the embodiments of FIGS. 3A and 3B, respectively.
Figure 5B:
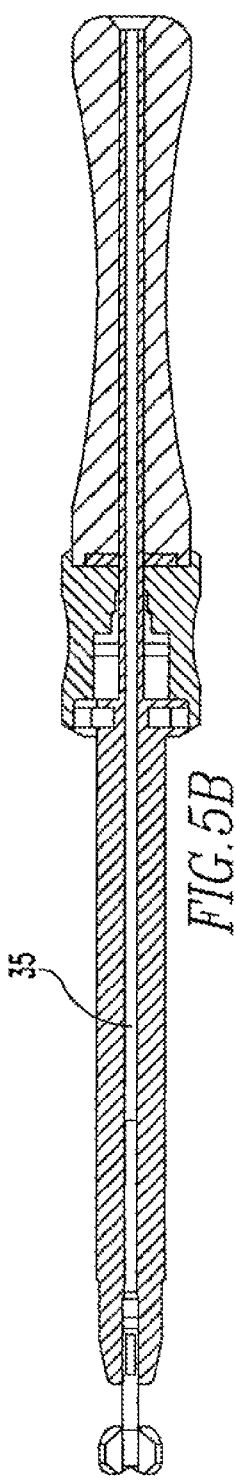
Figure 6B:
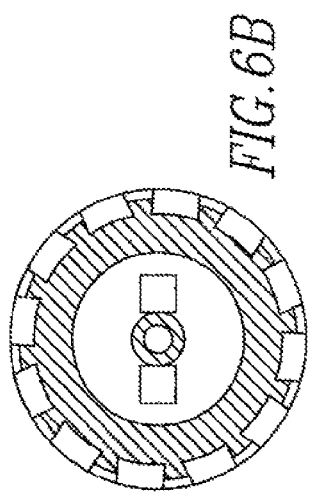
FIGS. 6A-B are sectional views along the lines B-B and C-C of the embodiments of FIGS. 3B and 3A, respectively.
Figure 6A:
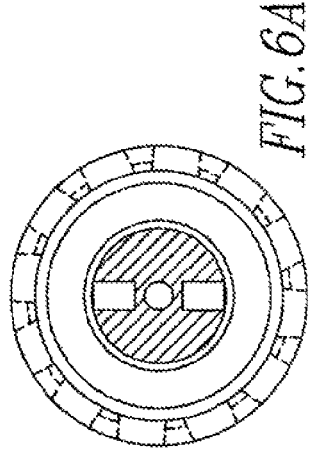

Referring to FIG. 1, there is shown a lateral view of a right shoulder 10 featuring the clavicle 11, acromion 12 and scapula 13. As illustrated, the shoulder 10 has undergone a Laterjet procedure to reduce the tendency of the joint to dislocate. During this procedure, the tip of the coracoid process 14 has been removed and transferred to the front of the glenoid 15. The stump of the coracoid process 20 from which the tip 14 has been removed can clearly be seen superior to the point of attachment to the glenoid 15. The tip of the coracoid process 14 has been drilled during the process of its removal, and the channel thus formed aligned with a corresponding channel formed in the glenoid 15 prior to the insertion of screw 21 to secure the tip to the glenoid. In a typical procedure, the channel in the glenoid is formed prior to the procedure to remove the tip of the coracoid process. As can be seen, the tip of the coracoid process has been removed, transferred and secured, along with the conjoined tendon, to the glenoid rim.

FIGS. 2 to 11 illustrate a surgical instrument in accordance with one embodiment of the present invention. There is shown an elongate surgical instrument 22 comprising a body which includes a shaft 23, in which the shaft comprises a handle 24 at a proximal end and a head 25 at a distal end.

Head 25 includes a mouth (30 of FIGS. 3B and 4B) and a jaw assembly formed from a pair of arms 31.

Mouth 30 defines the distal end of lumen 35 (FIGS. 4A, 4B, 5A and 5B), which extends along the longitudinal axis of instrument 22, through shaft 23 and handle 24, exiting at the proximal end of the handle 40.

In addition, and more clearly seen in FIG. 8, mouth 30 includes engaging means 41 suitable for engaging with tissue such as bone. The engaging means 41 are located at the periphery of the mouth 30 and comprise one or more teeth. Typically, the mouth includes between two and six teeth, but may include more. The teeth help the instrument to grip to tissue and bone and prevent it from slipping over the surface. This is particularly important as it helps to ensure that the drill does not travel during the drilling process, which can cause unwanted fracture and splitting of bone and tissue.

Handle 24 comprises actuating means 28 for moving the jaw assembly between a first, open, position and a second, substantially closed, position, and intermediate positions therebetween. The actuating means 28 include a pair of elongate rods 29, the distal ends of which are pivotally attached to the proximal ends of the arms 31 of the jaw assembly, and are pivotally connected at their proximal ends with a threaded boss (not shown). The actuating means further include a cylindrical rotary knob 27. The surface of the inner wall of rotary knob 27 is threaded (not shown) and is complementary with that of the threaded boss attached to rods 29. Rotary knob 27 is co-axially mounted on the handle, and co-axially aligned with the lumen 35 of the instrument 22.

In the embodiment shown, the handle is co-axially aligned with the shaft of the instrument, however, it will be recognised that other handle arrangements can be used. For example, the instrument can include a hand- or pistol-grip which can also be used to operate the jaw assembly. Handle or pistol-grip arrangements will suitably include a ratchet mechanism.

These features mean the instrument is easy to handle and can be held and operated with one hand.

In the illustrated embodiment, the actuating means includes a pair of rods. However, in alternative embodiments, not shown, one, three or more rods are utilised to actuate the jaw assembly. In alternative embodiments, other suitable means for moving the jaw assembly can be used. For example, the jaw assembly can be actuated by one or more cables.

In FIG. 3B, the proximal ends of arms 31 are attached to rods 29, proximal to mouth 30 about pivot points 33 and 33'. In alternative embodiments, not shown, the point of attachment of the arms is adjacent or in front of the mouth.

As can be seen in FIG. 2, the distal end of each arm 31 includes a paddle 32. Paddles 32 also include one or more inwardly facing projections 34. In the view of the distal end of the surgical instrument of FIG. 4B, the paddles 32 and inwardly facing projections 34 collectively form an opening, coaxially with the longitudinal axis of the shaft, when the jaw assembly is substantially closed, or attached to tissue or bone and between the first and second positions. In use, this opening allows the distal end of a drill, or a drill-guide, which has been passed through the lumen 35 from the proximal end of the surgical instrument and which exits the mouth 30, to pass through the jaw assembly. This is important in situations where a surgeon wishes to drill beyond the closed jaw assembly as it means that the instrument can remain in place, and does not have to be removed, in order to continue drilling.

In preferred embodiments, the inwardly facing projections 34 have a U- or V-shaped cross-section in a plane perpendicular to the longitudinal axis of the shaft, when viewed when the jaw assembly is substantially closed. The shape of the projections allow the instrument to grip bone, such as the tip of the coracoid process, and centre the instrument to facilitate a drill to pass through its centre to prevent fracture and splitting of a subsequently taken graft. Other suitable shapes and designs of projection can be used and, where appropriate, different paddle and projection designs can be incorporated within a single instrument, for example to accommodate a particularly irregular-shaped bone or tissue.

Figure 11:
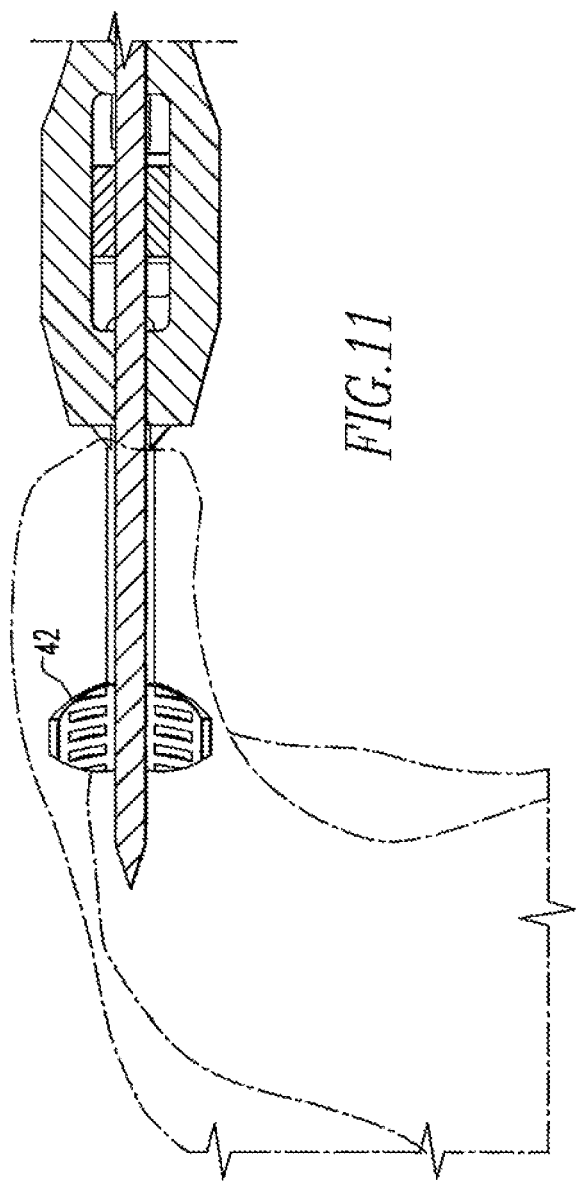
FIG. 11 is a sectional view through the longitudinal axis of the drill-guide of FIG. 10.

As shown in FIGS. 9 and 11, the inner surfaces of the projections 34 also include a gripping surface which can include a series of studs, serrations or ribs 42, or a combination thereof (not shown). The gripping surface further enhances the ability of the instrument to grip the bone or tissue.

In alternative embodiments, not shown, the arms of the jaw assembly are curved or scythe-like. The inside edges of the curved arms can have sharpened inner edges, although it is preferred that they are rounded to prevent unnecessary damage to the surface of the bone to which they may be attached. In such embodiments the arms typically have sharpened distal tips.

In further alternative embodiments, not shown, the arms of the jaw assembly can all consist of paddles or all sharpened distal tips, or any combination thereof. For example, a preferred alternative embodiment (not shown), which can be utilised for drilling the distal tip of the coracoid process in a Laterjet procedure, has two pairs of arms in which three arms are paddles and one arm is a sharpened distal tip. The pair of arms can be arranged substantially perpendicular to one another, with a first pair operating in the medial-lateral plane and the second pair operating the superior-inferior plane. In this particular embodiment, it is important that the arm which will be positioned inferiorly within the superior-inferior plane has a sharpened distal tip so that it can pass through the conjoined tendon to engage with the tip of the coracoid process.

In embodiments which are to be used specifically for procedures on the coracoid process a particularly preferred embodiment includes a jaw assembly comprising a single pair of arms is aligned medial-laterally.

Once closed, the jaws must be capable of being locked prior to drilling to prevent unwanted movement of the instrument and drill. The lock (not shown) can be achieved by a ratchet, locking screw or by the mechanical advantage of a screw thread Referring now to FIGS. 7 to 11, the surgical instrument is shown in use. In FIG. 7, the jaw assembly has been closed around the tip of the coracoid process 14 (shown with transparency), and a drill 43 passed into the tip. Prior to drilling, jaw assembly was positioned adjacent to the tip of the coracoid process and the actuating means used to close the jaw assembly around the tip. During this process, as the jaw assembly closes around the bone, the teeth around mouth 30 are brought into engagement with the distal tip of the coracoid to help prevent the jaw assembly from slipping. Alternatively, once the tip of the coracoid process has been identified a surgeon can press the mouth 30 and its teeth into the tip to give purchase to the instrument whilst the jaw assembly is closed.

In preferred embodiments, the drill includes a depth gauge or stop (not shown) to prevent a surgeon from drilling too deeply.

Although the surgical instrument is designed to be operated with one hand so that it can be used arthroscopically, it can also be used in a conventional open procedures.

Figure 12:
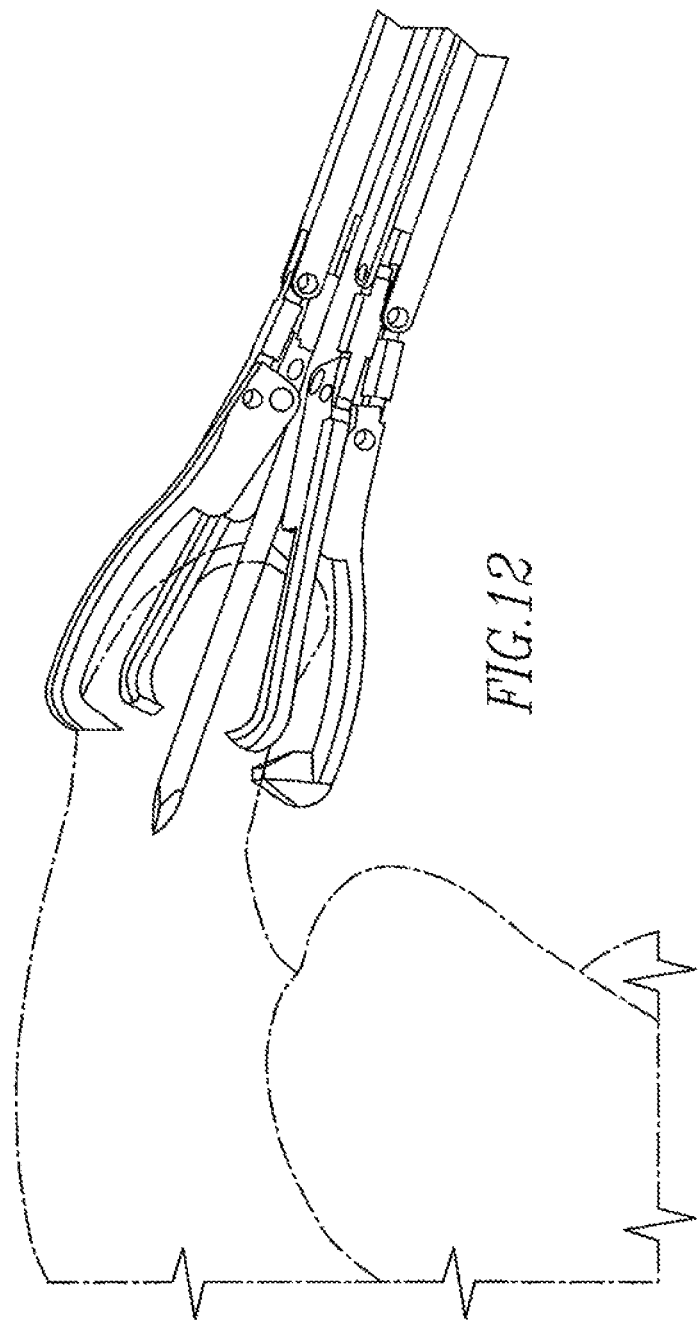
FIG. 12 is a second embodiment of a drill-guide according to the invention.

In an alternative embodiment shown in FIG. 12, the jaw assembly of the surgical instrument comprises two pairs of arms substantially perpendicular to each other, one pair grasping the coracoid in the medial-lateral plane, the other in the superior-inferior plane. As each pair of arms closes symmetrically along a central axis shared with the lumen extending through the instrument, the mouth of the instrument, and thus the drill-guide, centre on the tip of the coracoid process. A drill passed down the central lumen of the instrument will naturally pass through the centre of the coracoid at the point of contact and, as a result, will drill through its centre minimising any risk of fracture of the graft.

In embodiments featuring a second pair of arms, because the coracoid process is approximately 60% wider in the medial-lateral plane than in the superior-inferior plane, the medial-lateral arms contact the coracoid before the superior-inferior arms. To prevent damage to the coracoid process, the actuating means includes a compressible spring (not shown) which compresses until the superior-inferior arms contact the coracoid, at which point the actuating means drives both pairs of arms until they securely grip the coracoid process. The medial-lateral arms centre the axis of the drill and superior-inferior arms at the point of contact in the medial-lateral plane, and the superior-inferior arms centre the axis in the superior-inferior plane at the point of contact.

The invention claimed is:

1. A surgical instrument comprising:
   an elongate body comprising a shaft having a handle towards its proximal end and a head towards its distal end, the head comprising a mouth and a jaw assembly, wherein the jaw assembly comprises a pair of arms laterally offset from one another about a longitudinal axis of the shaft;
   an actuating mechanism positioned within an interior of the shaft and having a proximal end and a distal end, the actuating mechanism being adapted to move the arms of the jaw assembly between a first open position, a second substantially closed position, and intermediate positions therebetween, wherein the actuation mechanism is configured to cause each of the arms to rotate relative to the shaft along a different rotational axis; and
   a lumen aligned with a longitudinal axis of the shaft, extending from a proximal end of the surgical instrument to the mouth of the shaft, wherein the lumen is suitable for receipt and passage of a drill or drillpiece so as to enable the drill or drillpiece to pass through the jaw assembly;
   wherein the actuating mechanism is interposed between an interior surface of the shaft and an exterior surface of a wall defining the lumen.

2. The instrument according to claim 1, wherein the mouth further comprises engaging means suitable for engaging with the bone.

3. The instrument according to claim 2, wherein the engaging means are located at a periphery of the mouth.

4. The instrument according to claim 2, wherein the engaging means comprises one or more sharpened teeth.

5. The instrument according to claim 1, wherein the pair of arms are operable in a plane which passes through the longitudinal axis of the shaft.

6. The instrument according to claim 1, wherein the jaw assembly further comprises a second pair of arms distinct from the first pair of arms, wherein the arms include pin pivots and wherein each of the arms rotates along a different rotational axis.

7. The instrument according to claim 6, wherein the two pairs of arms of the jaw assembly are operable within different planes.

8. The instrument according to claim 7, wherein the two pairs of arms of the jaw assembly are operable within substantially perpendicular planes.

9. The instrument according to claim 1, wherein the arms of the jaw assembly each include an inner surface that curves or otherwise angles toward the longitudinal axis whereby the arms form a non-enclosed space between the arms even when the jaws are closed.

10. The instrument according to claim 1, wherein the arms include pin pivots and wherein one or more of the arms is an elongated prong having a sharpened distal tip.

11. The instrument according to claim 1, wherein each arm comprises a paddle at its respective distal end.

12. The instrument according to claim 11, wherein each paddle includes one or more inwardly facing projections.

13. The instrument according to claim 12, wherein the inwardly facing projections are substantially perpendicular to the longitudinal axis of the shaft when the jaw assembly is in the substantially closed position.

14. The instrument according to claim 12, wherein inner surfaces of the inwardly facing projections comprise gripping surfaces which includes a series of studs, serrations or ribs, or a combination thereof.

15. The instrument according to claim 11, wherein the arms include pin pivots and wherein the paddles collectively form a distal opening, coaxially with the longitudinal axis of the shaft, when the jaw assembly is closed so as to enable the drill or drillpiece to pass through the opening and extend distally from the jaw assembly even when the jaw assembly is closed.

16. The instrument according to claim 15, wherein inwardly facing projections form the opening.

17. The instrument according to claim 15, wherein the opening has a noncontinuous border.

18. The instrument according to claim 11, wherein the paddles are anatomically shaped to conform with contours of a bone at respective areas of engagement for gripping the bone with the jaw.

19. The instrument according claim 11, wherein inner surfaces of each paddle comprise gripping surfaces which includes a series of studs, serrations or ribs, or a combination thereof.

20. The instrument according to claim 1, wherein the actuating mechanism includes a plurality of rods.

21. The instrument according to claim 20, wherein the plurality of rods are driven by one or more levers in the form of a hand- or pistol-grip.

22. The instrument according to claim 20, wherein proximal ends of the plurality of rods are pivotally connected with a threaded boss and the plurality of rods are drivable by a rotary knob having a mating screw thread that is complementary with that of the threaded boss, and wherein the rotary knob is co-axially aligned with the lumen of the device.

23. The instrument according to claim 22, wherein the rotary knob is coaxially mounted with the handle.

24. The instrument according to claim 1, wherein the jaw assembly further comprises a lock to lock the jaw assembly in one of the first, second, and intermediate positions.

25. The instrument according to claim 24, wherein the lock comprises a ratchet, a locking screw, or screw thread.

26. The instrument according to claim 24, wherein the lock is self-locking and locks itself when the jaw assembly is closed around an object.

27. The instrument according to claim 1, wherein the actuating mechanism is driven by one or more levers in the form of a hand- or pistol grip.

28. The instrument according to claim 1, wherein the rotational axes are parallel to one another and laterally offset relative to the longitudinal axis.

29. A kit comprising:
and a drill or drillpiece; and
a surgical instrument for guiding the drill or drillpiece into bone, the surgical instrument comprising:
an elongate body comprising a shaft having a handle towards its proximal end and a head towards its distal end, the head comprising a mouth and a jaw assembly, the jaw assembly comprising a pair of opposed reciprocating arms;
a lumen aligned with a longitudinal axis of the shaft, extending from a proximal end of the surgical instrument to the mouth of the shaft, wherein the lumen is suitable for receipt and passage of the drill or drillpiece so as to enable the drill or drillpiece to pass through the jaw assembly; and
a plurality of rods aligned with the longitudinal axis of the shaft and positioned within an interior of the shaft, wherein distal ends of the plurality of rods are attached to proximal ends of the arms of the jaw assembly at respective pin-pivots;
wherein the plurality of rods are adapted to move the jaw assembly between a first open position, a second substantially closed position, and intermediate positions therebetween.

30. The kit according to claim 29, wherein the drill is retractable.

31. The kit according to claim 29, wherein the drill has distal and proximal ends and is engageable with a powered drive-unit at its proximal end.

32. The kit according to claim 29, wherein the drill is moveable from a first position, in which a distal end of the drill is located in the shaft, to a second position, in which the distal end of the drill extends from the mouth.

33. The kit according to claim 29, wherein the drill comprises a depth gauge or stop.

34. A kit comprising:
a drill or drillpiece; and
a surgical instrument, comprising:
an elongate body comprising a shaft having a handle towards its proximal end and a head towards its distal end, the head comprising a mouth and a jaw assembly, wherein the jaw assembly comprises a pair of arms laterally offset from one another about a longitudinal axis of the shaft, wherein the arms include pin pivots;
a lumen aligned with the longitudinal axis of the shaft, extending from a proximal end of the surgical instrument to the mouth of the shaft, wherein the lumen is suitable for receipt and passage of the drill or drillpiece so as to enable the drill or drillpiece to pass through the jaw assembly; and
an actuating mechanism positioned within an interior of a tubular portion of the shaft and having a proximal end and a distal end, the actuating mechanism being adapted to move the arms of the jaw assembly between a first open position, a second substantially closed position, and intermediate positions therebetween.

* * * * *